(12) United States Patent
Mallinson et al.

(10) Patent No.: US 9,808,181 B2
(45) Date of Patent: Nov. 7, 2017

(54) SYSTEM AND METHOD FOR IN-RUMEN MONITORING

(75) Inventors: Paul Benjamin Mallinson, Auckland (NZ); Jose Alberto Laporte-Uribe, Auckland (NZ)

(73) Assignee: Kahne Limited, Auckland (NZ)

( * ) Notice: Subject to any disclaimer, the term of this patent is extended or adjusted under 35 U.S.C. 154(b) by 620 days.

(21) Appl. No.: 14/126,577

(22) PCT Filed: Jun. 15, 2012
(Under 37 CFR 1.47)

(86) PCT No.: PCT/NZ2012/000100
§ 371 (c)(1),
(2), (4) Date: Aug. 14, 2014

(87) PCT Pub. No.: WO2012/173502
PCT Pub. Date: Dec. 20, 2012

(65) Prior Publication Data
US 2015/0230727 A1    Aug. 20, 2015

(30) Foreign Application Priority Data

Jun. 16, 2011 (NZ) ........................................ 593497

(51) Int. Cl.
*A61B 5/00* (2006.01)
*A61B 5/07* (2006.01)
(Continued)

(52) U.S. Cl.
CPC ................ *A61B 5/073* (2013.01); *A61B 5/01* (2013.01); *A61B 5/036* (2013.01); *A61B 5/0538* (2013.01);
(Continued)

(58) Field of Classification Search
CPC .............................. A61B 5/073; A61B 5/4238
See application file for complete search history.

(56) References Cited

U.S. PATENT DOCUMENTS

| | | | |
|---|---|---|---|
| 5,984,875 A | * | 11/1999 | Brune .................. A01K 11/007 119/174 |
| 6,099,482 A | | 8/2000 | Brune et al. |

(Continued)

FOREIGN PATENT DOCUMENTS

| | | | |
|---|---|---|---|
| EP | 0507629 | 10/1992 | |
| WO | WO 2011069105 A2 * | 6/2011 | ............... C12P 5/02 |

OTHER PUBLICATIONS

M. Richter et al., "The effect of individuality of animal on diurnal pattern of pH and redox potential in the rumen of dry cows," Czech. J. Anim. Sci., 55, 2010 (10):401-407.

*Primary Examiner* — John R Downey
(74) *Attorney, Agent, or Firm* — Dann, Dorfman, Herrell and Skillman, P.C.

(57) ABSTRACT

A system for monitoring digestive efficiency within the rumen of one or more ruminant animals comprises rumen boluses shaped and sized to be retained within the rumen dorsal sac and each comprising temperature, pH sensor, and redox sensors, and a wireless transmitter. A processor is arranged to derive from the sensor data one or more parameters indicative of animal digestive efficiency including any combination of one or more of hydrogen scale (rH), partial pressure of hydrogen ($pp[H_2]$), oxygen fugacity ($f(O_2)$) and free energy of the system ($\Delta G$). A method and bolus are also claimed.

20 Claims, 6 Drawing Sheets

(51) Int. Cl.
*A61B 5/01* (2006.01)
*A61B 5/145* (2006.01)
*A61B 5/03* (2006.01)
*A61B 5/053* (2006.01)

(52) U.S. Cl.
CPC ...... *A61B 5/14503* (2013.01); *A61B 5/14539* (2013.01); *A61B 5/14546* (2013.01); *A61B 5/4255* (2013.01); *A61B 5/7225* (2013.01); *A61B 5/7278* (2013.01); *A61B 2503/40* (2013.01); *A61B 2562/08* (2013.01); *A61B 2562/162* (2013.01)

(56) References Cited

U.S. PATENT DOCUMENTS

| | | | |
|---|---|---|---|
| 2002/0128542 A1 | 9/2002 | Van Over | |
| 2004/0133131 A1* | 7/2004 | Kuhn | A01K 11/007 600/593 |
| 2008/0182309 A1* | 7/2008 | Vlad | C12M 35/02 435/161 |
| 2008/0236500 A1* | 10/2008 | Hodges | A01K 11/007 119/14.02 |
| 2009/0048498 A1* | 2/2009 | Riskey | A61B 5/0031 600/302 |
| 2009/0182207 A1* | 7/2009 | Riskey | A61B 5/0031 600/302 |
| 2009/0187392 A1* | 7/2009 | Riskey | A01K 11/007 703/11 |
| 2012/0088988 A1* | 4/2012 | Sato | A01K 11/007 600/302 |
| 2012/0100591 A1* | 4/2012 | Kohn | C12P 5/02 435/167 |
| 2014/0338447 A1* | 11/2014 | Sharpe | A01K 29/005 73/431 |

* cited by examiner

SYSTEM AND METHOD FOR IN-RUMEN MONITORING

FIELD OF INVENTION

The invention relates to a device, system, and method for monitoring the physiological condition of a ruminant, and in particular a rumen bolus for cattle and to methods of utilising the bolus data to provide information relevant to a one or more application.

BACKGROUND

A rumen bolus is a device that is ingested into the rumen (stomach) of an animal, such as a cow or sheep for example, for monitoring the physiological state of the animal.

Kahne Ltd has developed a wireless rumen bolus that monitors in-rumen Ph, temperature, and pressure (see www.kahneanimalhealth.com). The bolus can transmit data in real time or at a specific time of day, which is received by the end user in raw format. The bolus is mainly used as a scientific instrument for those involved in rumen research. It assists scientists by providing a continuous and real-time flow of in vivo measurements from cattle living under realistic commercial conditions. However, it is currently still left up to the scientist to analyse the raw data from the bolus and make sense of what it represents.

SUMMARY OF THE INVENTION

The invention provides an improved or at least alternative system, method, and/or bolus for in-rumen monitoring.

In one aspect the invention may broadly be said to consist of a system for monitoring digestive efficiency within the rumen of one or more ruminant animals comprising:
  one or more rumen boluses each shaped and sized to be retained within, or residing within, the dorsal sac of the rumen of the associated animal and each comprising:
    a temperature sensor to provide data indicative of temperature within the rumen,
    a pH sensor to provide data indicative of pH within the rumen,
  a redox sensor to provide data indicative of the oxidation-reduction potential within the rumen, and
    a wireless transmitter to transmit data or derived parameter(s) to a remote station, and
  in the or each bolus or at a remote station a processor arranged to derive from the sensor data one or more parameters indicative of animal digestive efficiency.

Preferably the system comprises a bolus for or residing in the rumen of a sub population of a group of animals. The group of animals may be any animal management grouping such as a mob or herd, and may comprise a herd of twenty or fifty or more animals. The sub population may be any number of animals within the group from a single animal to all of the animals. The system may comprise a bolus for or residing in the rumen of many or a majority or all of a multiple number of animals of such a group of animals. Each bolus may comprise stored in memory in the bolus an identification code unique to the individual bolus.

Preferably the system is arranged to transmit data at least once, or twice, or more times per week or day for at least one, two, or four weeks, or one, three, or six months, or indefinitely.

Preferably the processor is associated with memory storing one or more thermodynamic and/or physiological equations, the processor arranged to input the sensor array data into one or more or all of the equations to obtain as outputs the one or more parameters indicative of animal digestive efficiency.

The processor may be located within a remote station and the sensor data transmitted to the remote station. Alternatively the processor may be located within the or each bolus and the data transmitted to the remote station is the one or more parameters indicative of animal digestive efficiency.

In a second aspect the invention may broadly be said to consist of a method for monitoring digestive efficiency of the rumen of one or more ruminant animals comprising the steps of:
  providing a bolus within the dorsal sac of the rumen of the or each animal,
  sensing a combination of temperature, pH, and oxidation-reduction potential within the dorsal sac of the or each rumen,
  wirelessly transmitting the sensed data to a remote receiver, and
  in a processor in the or each bolus or at a remote station deriving from the sensor data one or more parameters indicative of animal digestive efficiency.

Preferably the method comprises providing a bolus within the dorsal sac of the rumen of many or a majority or all of a multiple number of animals such as a herd of fifty or more animals. Each bolus may comprise stored in memory in the bolus an identification code unique to the individual bolus.

Preferably the method comprises uploading or transmitting data at least once, or twice, or more times per week or day for at least one, two, or four weeks, or one, three, or six months, or indefinitely.

Preferably the one or more parameters indicative of animal digestive efficiency includes any combination of one or more of hydrogen scale (rH), partial pressure of hydrogen ($pp[H_2]$), oxygen fugacity ($f(O_2)$), and free energy of the system ($\Delta G$).

Preferably the equation stored in memory for obtaining rH is:

$$rH = (E_h * 2 * F/(2.303 * R * T)) + 2 * pH$$

where:
$E_h$ = Hydrogen potential (V) derived from the redox sensor data
F = Faraday's constant (96.485 kJ·V$^{-1}$·mol$^{-1}$)
R = gas constant (0.008314472 kJ·mol$^{-1}$·K$^{-1}$)
T = temperature (K) derived from the temperature sensor data,
rH = -log ($H_2$), and
pH = -log ($H^+$) derived from the pH sensor data.

Preferably rH is indicative of the reductive or oxidative intensity of the rumen environment and the processor is arranged to output a value ranging from 0 to 42, wherein 0 represents a saturated atmosphere of hydrogen.

Preferably the equation stored memory for obtaining $pp[H_2]$ is:

$$pp[H_2] = 10^{-rH} \text{ (atm)}$$

where:
$pp[H_2]$ = partial pressure of hydrogen (atmospheres), and
rH = hydrogen scale.

Preferably the equation stored in memory for obtaining $f(O_2)$ is:

$$\text{Log } f(O_2) = [((E_h - 0.818) * 4 * F/(2.303 * R * T)) + 4 * pH]$$

where:
$f(O_2)$ = fugacity of oxygen gas ($p[O_2]$)
$E_h$ = hydrogen potential (V) derived from the redox sensor data F=faraday's constant (96.485 kJ·V$^{-1}$·mol$^{-1}$)
R=gas constant (0.008314472 kJ·mol$^{-1}$·K$^{-1}$)
T=temperature (K) derived from the temperature sensor data, and
pH=−log (H$^+$) derived from the pH sensor data.

Preferably the equation stored in memory for obtaining ΔG is:

$$\Delta G = 2.303 * R * T * rH$$

where:
ΔG=the free energy of the system (kJ/mol$^{-1}$)
R=gas constant (0.008314472 kJ·mol$^{-1}$·K$^{-1}$)
T=temperature (K) derived from the temperature sensor data, and
rH=the hydrogen scale.

In a third aspect the invention may broadly be said to consist of a rumen bolus for a ruminant animal, comprising:
a body shaped and sized to be retained within the dorsal sac of the rumen of the animal,
housed within the body of the bolus:
a temperature sensor to provide data indicative of the temperature within the rumen,
a pH sensor to provide data indicative of the pH within the rumen,
a redox sensor to provide data indicative of the oxidation-reduction potential within the rumen,
a wireless transmitter to transmit the read sensor array data or one or more parameters derived by processing the data, or both, to a remote station.

In some embodiments the bolus also comprises a processor and memory associated with the processor storing one or more thermodynamic and/or physiological equations, the processor arranged to input the sensor array data into one or more or all of the equations to obtain as an output one or more parameters indicative of animal digestive efficiency.

The term "comprising" as used in this specification means "consisting at least in part of". When interpreting each statement in this specification that includes the term comprising", features other than that or those prefaced by the term may also be present. Related terms such as "comprise" and "comprises" are to be interpreted in the same manner.

BRIEF DESCRIPTION OF THE DRAWINGS

The invention is further described, by way of example only, and with reference to the drawings, in which.

DETAILED DESCRIPTION OF PREFERRED EMBODIMENTS

Figure 1:
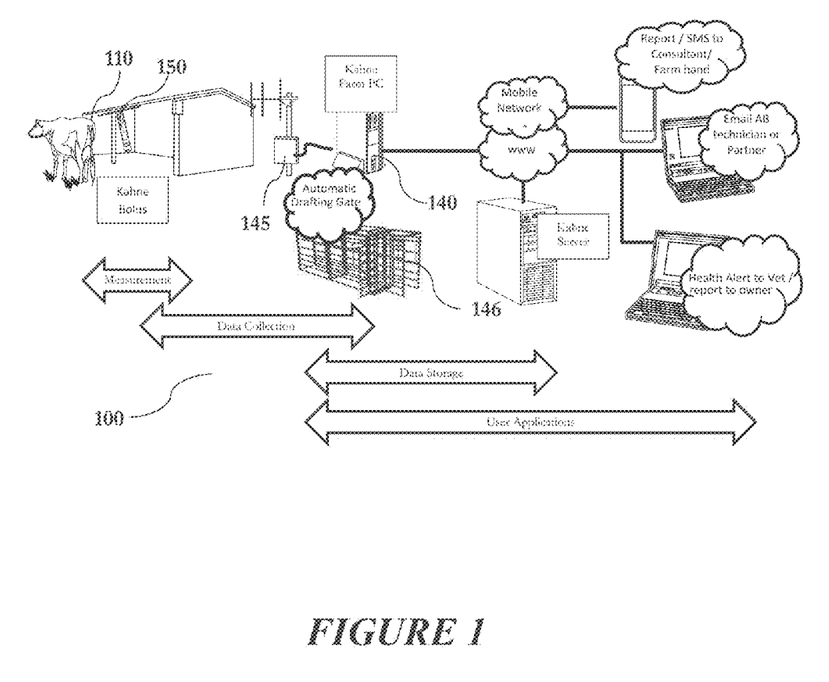
FIG. 1 shows a system of the invention for monitoring the rumen environment in a plurality of animals.

Referring to FIG. 1, a preferred embodiment system 100 for monitoring the rumen environment of one or more ruminant animals such as cows and in particular in-rumen digestive efficiency comprises a bolus 150 residing in the rumen of an animal 110 (one only shown) or of many or a majority of or all of a multiple number of animals such as a herd of twenty or fifty or more animals, and a remote server comprising a computer processor 140 for receiving and processing data sent from the or each bolus 150. The data is analysed for each animal to determine the efficiency of feed conversion and/or bacterial activity. The system 100 is described with reference to cattle 110 but may also be used with other ruminant animals however.

Each bolus 150 is swallowed/ingested by a cow 110 into the stomach where it resides in the dorsal sac of the rumen of the cow 110. The rumen environment is monitored by the bolus 150 which senses the temperature, pH and, oxidation-reduction (redox) state/potential in the rumen. The bolus 150 may send the data in raw format to remote server 140 which performs the processing and analysis to derive one or more parameters indicative of digestive efficiency, and/or an on-board processor in the bolus 150 may carry out such processing and transmit the derived parameters, or alternatively again the on-board processor may carry out some pre-processing before sending data to the server 140 for further processing. The bolus 150 communicates to the server 140 through wireless telemetry.

Figure 2:
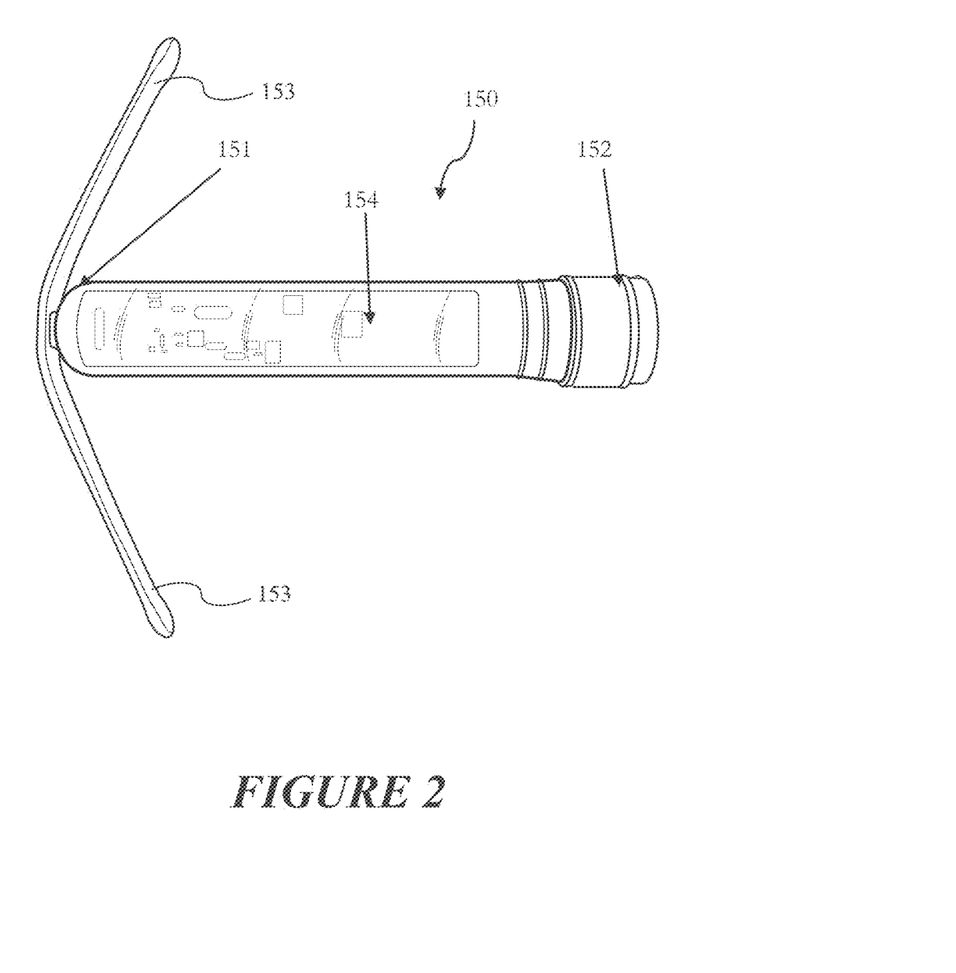
FIG. 2 is a perspective view of a rumen bolus of the system of FIG. 1

Referring now to FIG. 2, a preferred embodiment bolus 150 comprises a hollow body or housing 151 for retaining the various components of the bolus 150 and is shaped/sized to be retained within the dorsal sac of the rumen of the animal. The bolus comprises an elongate body of for cattle length in the range 135 to 160 mm and circular cross-section of diameter in the range 25 to 35 mm. At or towards one end the bolus comprises opposed lateral extensions or tabs 153, which are flexible towards the body of the bolus but have memory towards a position extending outwardly of the bolus body and slightly rearwardly (as shown), so that the tabs 153 may be forced against their memory towards the body of the bolus, manually or by a purpose administration tool, while the bolus is inserted down the throat of an animal with the outer ends of the tabs 153 trailing, but will restore to their outwardly extending position when the bolus reaches the dorsal sac of the rumen to hold the bolus in the dorsal sac. The bolus has light weight, preferably less than 100 grams, which along with buoyancy further assists it to be retained within the dorsal sac and not to fall through to the bottom of the rumen.

Fermentation in the rumen produces gas that is trapped within the mat, resulting in retention of large particles of grass and feed (greater than 2 mm) within in the dorsal sac. Liquid and smaller particles are deposited in the bottom of the rumen (ventral sac). Contained within the housing 151 are sensors exposed in use through the sensor head 152 to the rumen environment, including at least temperature, pH, and redox sensors. In the preferred embodiment a processor 154 within the bolus is connected to the sensors and periodically or continuously reads the sensor outputs and either processes the data to derive parameters indicative of digestive efficiency for the animal and sends same to the computer 140 or sends raw or pre-processed data to the computer 140, via a wireless transmitter also in the bolus. A battery is also provided onboard the bolus for supplying power to the sensors, microprocessor, and transmitter. The processor 154 may relay the information onto the transmitter immediately upon reading of the sensor outputs or in the preferred embodiment log the data for a certain period (i.e. between milking) and then send multiple sensor output readings in one transmission for the computer to then separate and process. Additionally, the information may be averaged and the values of the average and standard deviation stored to be transmitted. Any other suitable statistical or averaging scheme may be used before storing averaged sensor data however. It is from these obtained parameters that end applications can make use of the system 100 to improve the overall efficiency of the animal.

As stated data analysis may be carried out remotely or within the bolus itself and preferably comprises at least a processor for running the algorithms, memory for storing algorithms and data, and interface circuitry. The processor may be any form of programmable hardware device, whether a CPU, Digital Signal Processor, Field-Programmable Gate Array, Microcontroller, Application-Specific Integrated Circuit, or the like.

As stated and referring again to FIG. 1, the computer 140 in the preferred embodiment is arranged to receive and process data from a number of boluses 150 in a collection of livestock in a farm for example. Each bolus has stored in memory associated with the on board processor an identification code unique to the particular bolus 150. The unique ID is sent to the computer 140 with the sensor data or parameters to associate the information with the particular animal.

Each bolus 150 may also be arranged to transmit data or parameters to more than one computer 140, each computer arranged to process the bolus data or parameters in a particular way for a particular application or applications. Data analysis may be implemented on any suitable computer hardware system, platform or architecture.

In the preferred embodiment the sensor output readings and optionally the thermodynamic parameters are stored locally on the bolus device and uploaded (for the avoidance of doubt, in this specification and claims transmitting includes uploading) to the computer 140 automatically when the animal comes into proximity of a receiver device 145 installed in an appropriate location such as a milking shed, watering trough, crush, race or similar animal handling facility (animal milking, watering or handling station) for example.

Uploading or transmission of data or parameters may occur at least once, or twice, or more times per week or day for at least one, two, or four weeks, or one, three, or six months, or indefinitely. As shown in FIG. 1, animals may pass through the milking shed twice daily and the information from each bolus is collected and uploaded to computer or server 140.

The data is analysed for each animal to determine the efficiency of feed conversion and/or bacterial activity. Data analysis is described in further detail below. Information may be stored in a database associated with computer 140 or in any other type of digital storage medium (i.e. cloud based systems). Field applications can be developed to use this information to aid farmers to enhance animal performance, improve animal welfare, and/or reduce waste products or digestive efficiency. In turn productivity and health dynamics from within the rumen, where fermentation occurs, converting feedstuff to energy needed for milk production or muscle mass development, may be monitored and managed. Monitoring may occur over an extended period such as at least one, two, or four weeks, or one, three, or six months, or indefinitely until the animal carrying a bolus dies.

Animals beginning to suffer health issues will undergo changes to their physiology well before they exhibit external symptoms, which can be detected. Temperature is a basic indicator of animal health and can be used to diagnose sub clinical and clinical disease, heat stress, mastitis, metabolic disorders, reproductive cycles and even the impending birth of calves. With better rumen function management, farmers can expect to see a reduction in afflictions such as laminitis and high somatic cell counts which also adversely affect animal productivity.

Rumen function and efficiency are reflected in temperature as well as in pH changes throughout the digestive process of rumination. During digestion, rumen pH can vary from about 7.0 (neutral) to less than 5.0 (acidic), ideally maintaining a healthy neutral balance as much of the time as possible. Rumen microbes work best between pH 6-7. Efficiency of rumen fermentation is compromised when pH drops for a prolonged period. When diets contain excessive levels of rapidly degradable starch or sugars and not enough slow fermenting fibre, an overly acidic environment develops and pH can fall to around pH 5.5 and remain there. This has detrimental implications for both productivity and animal health and is a major challenge for both the dairy and feedlot industries around the world. Dairy herds experiencing this condition, often referred to as sub-acute ruminal acidosis (SARA), will have a decreased efficiency of milk production, increased waste (effluent, methane etc.), impaired cow health and high rates of involuntary culling. In addition up to 20% of dairy cows develop acidosis after calving. SARA can lead to more serious health issues, and if left untreated can progress to acute ruminal acidosis, defined as pH<5.0, which often results in death. It also predisposes the cow to more serious diseases such as lameness, mastitis and sub-fertility which can cost hundreds of dollars per affected animal.

Server 140 may be arranged to monitor pH continuously and produce alerts to a farmer when pH drops to an unhealthy level, allowing the farmer to make small changes in animal diet to stabilise pH and create a better rumen environment for more hours of the day, thus having a healthier, higher producing animal.

Server 140 may be wire or wirelessly linked to a controller of an automatic drafting gate 146 whereby animals with abnormal profiles may be automatically drafted to a holding pen, and optionally also an email alert sent by server 140 to the vet, farmer, technician or other advisor such as an animal nutritional consultant. Optionally again functionality may be provided enabling the vet, farmer, technician or nutritional consultant to log on to server 140 via the Internet and review the data, and for example assess if an on-site visit is required. At the end of each milking operation a summary report of the herd may be sent to the vet, farmer, technician or nutritional consultant identifying any individual outliers and animals of concern.

The ability of the system to provide long term 24/7 monitoring of the sensed data and calculated thermodynamic parameters provides the animal manager with a detailed picture of diurnal patterns and the effects changes in feed composition and feed management practice on the rumen environment. This enables the rumen environment to be actively managed on either a herd of individual animal basis thereby improving the efficiency of the animal at converting feed input to useful output (for example milk or meat). Maintaining ruminal pH, redox, ΔG etc. at optimal levels favours the growth of the beneficial microbes which synthesise VFAs and ATP which are absorbed by the ruminant through the rumen wall and are used in the creation of milk and muscle tissue. Outside optimal conditions production of less desirable microbes which are linked to the production of methane and other waste products increases. The consumption of feed by these undesirable microbes represents a direct loss of energy available to the beneficial microbes and, through their production of VFAs and ATP therefore, a direct loss of production of milk and meat.

Animal feeds are not homogenous and their different compositions in terms of protein, fibre, carbohydrates and sugars along with variations in particle size all influence the speed at which fermentation in the rumen may occur and therefore the degree and duration of changes in pH, temperature, redox and subsequent calculated thermodynamic parameters. The ability to measure these parameters combined with controlled feeding regimes provides the animal manager with a mechanism to influence the efficiency of the fermentation process in the rumen and the overall efficiency of the animal or animals.

The bolus may optionally also comprise pressure, conductivity, sodium, potassium, chloride and ammonium sensors. The data may optionally be analysed for each animal to determine one or more of the flow rate of digesta, rumen volume, methane production, mineral profile and volatile fatty acid profiles.

Data Analysis

The laws of thermodynamics (preferably alongside physiological equations) are applied to the data from the sensors to generate one or more parameters that can be used to interpret the efficiency of feed conversion/bacterial activity of the rumen. Physiological data read directly from the sensors or after processing physiological/thermodynamic equation outputs may give important information of the wellbeing of the animal and help to understand or predict diseases or metabolic syndromes. As stated the bolus 150 comprises a pH sensor, a redox sensor, and a temperature sensor, and is positioned in the dorsal sac of the rumen. Thermodynamic law may be applied to the sensor outputs to derive rH, pp[$H_2$], f($O_2$) and ΔG as shown below. These parameters are derived to monitor the bacterial activity within the rumen.

The Hydrogen Scale

The hydrogen scale, rH, gives a good indication of the reductive or oxidative intensity or potential of the rumen environment, analogous to the pH measurement of acidity or alkalinity. The rH scale integrates the pH and $E_h$ measurements giving a better description of the anaerobic microbial metabolism. For the same reason, it can be used in in vivo conditions to provide a direct indication of the oxidation/reduction state or potential of the rumen contents.

Given $$E_h = E_0 + 2.303 * R * T / n * F * (rH - 2 * pH)$$

rH is equal to:

$$rH = (E_h * 2 * F / 2.303 * R * T) + 2 * pH$$

where:
$E_h$=hydrogen potential (V) derived from the redox sensor output $E_o$=the potential of the reaction, in this case 0 (hydrogen potential)
n=number of electron in the reaction, in this case 2
F=faraday's constant (96.485 kJ·$V^{-1}$·$mol^{-1}$)
R=gas constant (0.008314472 kJ·$mol^{-1}$·$K^{-1}$)
T=temperature (K) derived from the temperature sensor output
rH=−log ($H_2$), and
pH=−log ($H^+$) derived from the pH sensor output.

The scale spans from 42 to 0, where 0 represents a saturate atmosphere of hydrogen (1 atmosphere). Values of different oxidation-reduction reaction can be stated in that scale and for every two species of reactants a certain value of ΔrH applies. This may be used to observe reaction couples (reactant: product) to a specific redox capacity and predict the efficiency of that particular reaction.

Partial Pressure of $H_2$

There is a close relationship between changes in hydrogen gas ($H_2$) concentration in the gas phase and rH scale in the rumen liquor. Indeed, rH scale also represents the hydrogen gas partial pressure by the formula already discussed. $H_2$ not only is a key intermediary in the degradation of organic matter in the rumen, but hydrogen partial pressure (pp[$H_2$]) in the rumen gas cap can be directly linked to the methane production in in vitro conditions. Interspecies $H_2$ transfer drives biochemical reaction such as the production of short chain fatty acids (SCFA) and energy formation (ATP). Furthermore, monitoring pp[$H_2$] in real-time enhances knowledge of the carbohydrate fermentation processes (SCFA, ATP and methane formation) and interspecies $H_2$ transfer leading to the optimisation of fermentative processes and reducing methane losses.

The hydrogen scale (rH) is the negative logarithm in base 10 of the hydrogen partial pressure, therefore:

$$rH = -\log pp[H_2]$$

then, $$pp[H_2] = 10^{-rH} \text{ (atm)}$$

where:
pp[$H_2$]=partial pressure of hydrogen (atmospheres), and,
rH=Hydrogen scale.

At a value of 0 rH the partial pressure of hydrogen is 1 atmosphere

Oxygen Fugacity (f($O_2$))

Increasing oxygen pressure (f($O_2$)) in the rumen liquor has been related to reduction in methane emissions and causes free $H_2$ to accumulate in the fluid. Conversely, low f($O_2$) tension, observed after feeding increases methane production. It has been shown that rumen protozoa are important scavengers of dissolved oxygen (Ellis et al. 1989). Then, the fate of f($O_2$) observed after feeding could be a good indicator of protozoa activity. Protozoa activity in the rumen has been linked to the rate of nitrogen turnover, therefore dietary changes will enhance protozoa activity increasing nitrogen turnover. Similarly, the symbiosis between protozoa and methanogens could protect methanogens from high ruminal oxygen concentrations. In essence, monitoring f($O_2$) helps in the interpretation of variation in methane emissions due to the protozoa activity.

On the other hand, monitoring f($O_2$) is associated to conversion of lactate into propionate through the acrylate pathway. Below the equilibrium (−50.16 of the log f($O_2$)) the formation of propionate will be favoured and above that equilibrium lactate will accumulate. In essence, f($O_2$) could help to optimise rumen fermentation by reducing the incidence of lactic acidosis or monitor the conversion of lactate to propionate.

The fugacity of the rumen is the log of the oxygen partial pressure and it is related to the potential of the hydrogen electrode by:

$$E_h = E_o + 2.303 * R * T/n * F * \text{Log}([\text{product}]/[\text{reactants}]).$$

and, $$E_h = E_o + 2.303 * R * T/4 * F * \text{Log}([O_2] * [H^+]^4 / [H_2O]^2)$$

In the rumen water [$H_2O$] is not limited in the reaction and the term could be obviated from the equation.

Therefore:

$$\text{Log } f(O_2) = [((E_h - 0.818) * 4 * F / (2.303 * R * T)) + 4 * pH)]$$

Where:

$f(O_2)$=fugacity of oxygen gas ($p[O_2]$)

$E_h$=hydrogen potential (V) derived from the redox sensor output $E_o$=the potential of the reaction (0.818 V)

n=number of electron in the reaction, in this case 4

F=faraday's constant (96.485 kJ·V$^{-1}$·mol$^{-1}$)

R=gas constant (0.008314472 kJ·mol$^{-1}$·K$^{-1}$)

T=temperature (K) derived from the temperature sensor output, and pH=−log ($H^+$) derived from the pH sensor output.

The fugacity of the oxygen gas in the rumen ($f(O_2)$) is represented in a logarithmic scale.

Gibbs Free Energy ($\Delta G$)

The systems energy is related to the rH scale by the following formula $$\Delta G = 2.303 * R * T * rH$$

where:

$\Delta G$=the free energy of the system (kJ)

R=gas constant (0.008314472 kJ·mol$^{-1}$·K$^{-1}$)

T=temperature (K) derived from the temperature sensor output, and rH=the hydrogen scale This formula is applied to systems involving 2 electrons $H_2 = 2H^+ + 2e$, as $rH = -\log[H_2]$. Because most of the reactions of interests in the rumen agree with that premise, the bolus 150 displays the $\Delta G$ of the system using that formula. However if the system where the free energy is related to the work required to expand half mole of hydrogen from steady state conditions to the required state, hence n=1, the value of rH needs to be replaced by rH/2.

By estimating the stoichiometry of carbohydrate fermentation values of ATP and SCFA formation can be estimated. SCFA is by ruminants the main source of energy for maintenance, growth and production. The conserved energy (ATP) is used mainly in the biosynthesis of cellular component, bacterial growth and multiplication. Although the efficiency of bacterial growth will depend on several mechanisms of energy dissipation, there seems to be an inverse relationship between the production of SCFA and microbial cell synthesis.

However, the limitations of these models are related to the minimal in vivo information about fluctuation in pH and $E_h$. The real time measurement of the thermodynamic parameters from the bolus will enhance our understanding of the rumen environment and give information of bacterial growth and nutrient formation.

The value Gibbs free energy of the rumen ($\Delta G$) represents the net or total energy of all reactions in the rumen:

$$\Delta G_{system} = \Sigma \Delta G_{reactions}$$

Additionally, $\Delta G$ of the system is the product of the enthalpy energy ($\Delta H$) realised during work (chemical reactions) and the entropy ($\Delta S$) of the system.

$$\Delta G_{system} = \Sigma \Delta H - \Sigma T \Delta S,$$

If $\Delta G = 0$, then $$\Sigma \Delta H = \Sigma T \Delta S$$

As the $\Delta G$ tends to equilibrium ($\Delta G = 0$) the enthalpy ($\Delta H$) and the entropy ($\Delta S$) of the system will tend to be equal and the reaction will not occur spontaneously.

Figure 5:
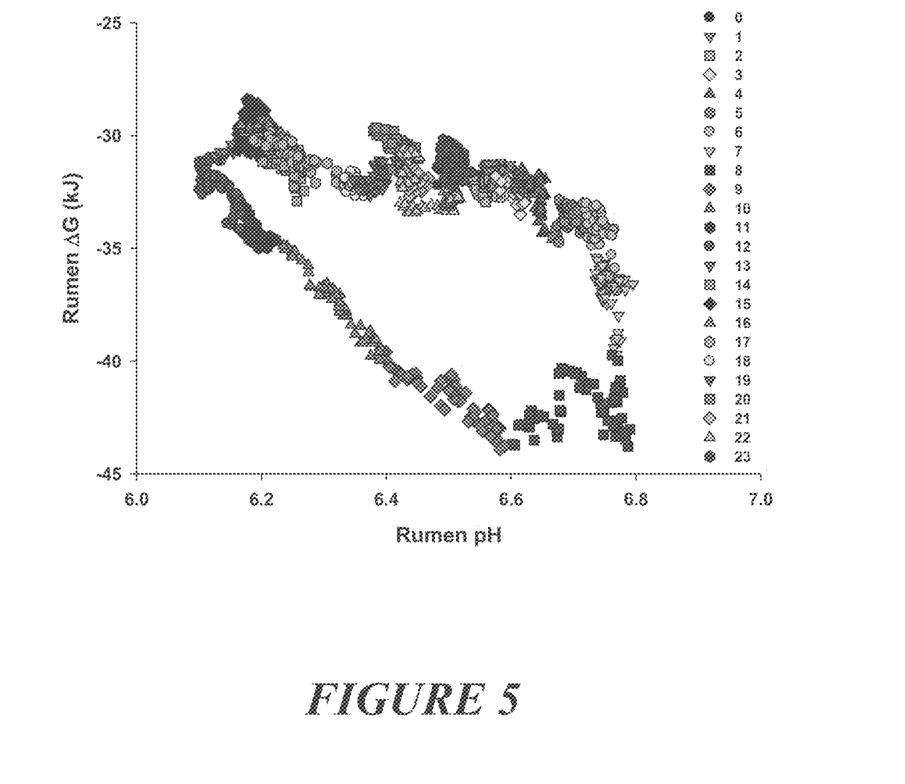
FIG. 5 is a graph obtained from the experimental work showing the relationship of the circadian rhythms of pH and free energy of the rumen (ΔG, kJ) in dry dairy cattle.

A decline in rumen pH also reflects the production and accumulation of SCFA. Therefore, as the rumen pH declines the $\Delta G$ should tend to equilibrium ($\Delta G = 0$). In FIG. 5 it can be see that after feeding around 8 am the rumen $\Delta G$ decline up to a maximum that maximum energy is related to the maximal potential work that the system can produce, the more negative the value the more potential work that the system can produce.

In similar way, the highest value of $\Delta G$ is reached 4-5 hours after this represent the maximal work that it can be done, this higher value of $\Delta G$ is correlated to the lowest pH, as we discussed the lowest the pH the higher the amount of SCFA produce.

With this technique it can be observed how food is digested and how much potential work can be done. Fermentation can be optimised by looking what feeding management or feed supplements provide animals with the best performance.

The following description of trials work further illustrates the invention.

Trial 1

Method: Two dry fistulated cattle were used in a Latin square design to test the reliability and accuracy of the bolus 150. Management of these animals include free access to drinking water and around 8 kg of dry matter intake per day. The daily pasture allowance was offered at around 8 AM daily. No attempts were made to change the dietary allowance or modify the daily managements.

Two boluses 150 were placed into the rumen through cannulae: one bolus in the dorsal sac and another attached to a 1.5 kg stainless steel weight to obtain data from the ventral sac. The boluses were set to log data every one minute for a 7 day period (one week).

After a period of one week the boluses were extracted, and placed in calibration solution (4, 7 and 10 and $E_h$ Zobell's solution) to test the drift of the pH and $E_h$ sensors. After this procedure the boluses were reallocated into the animals in a random fashion, and the process repeated at the end of each period (week) for 4 weeks. All the boluses recorded data at least once from both sites (dorsal or ventral) and from two animals (cow 1 and 2). Drift of the pH and $E_h$ sensor over a period of a month was assessed by testing the calibration recordings at the beginning of the experiment and at the end (week 4).

A full set of 6 days of recordings were used for the analysis. The data logged at the beginning of the week (set up) and at the of the week end (calibration) was discarded to avoid any disturbance of normal circadian rhythms during the days of manipulation, or $E_h$ changes due to cannula removal.

Figure 3A:
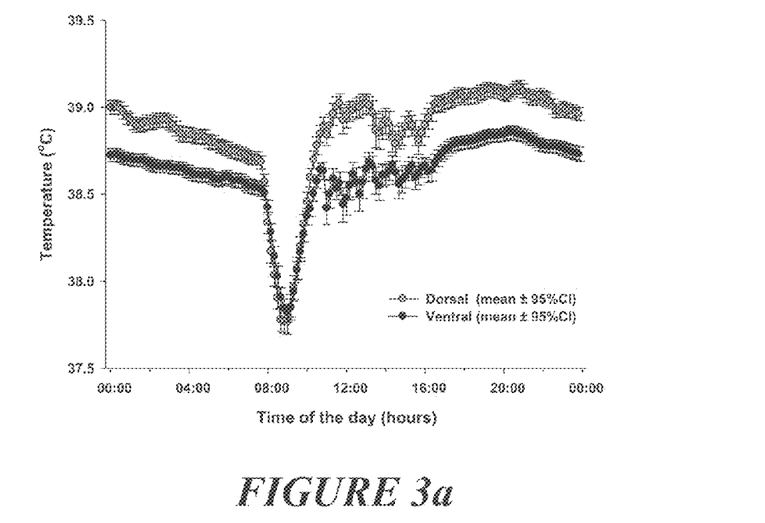
FIG. 3a is a graph obtained from the experimental work showing circadian rhythms of temperature from the ventral and dorsal sac of the rumen.
Figure 3B:
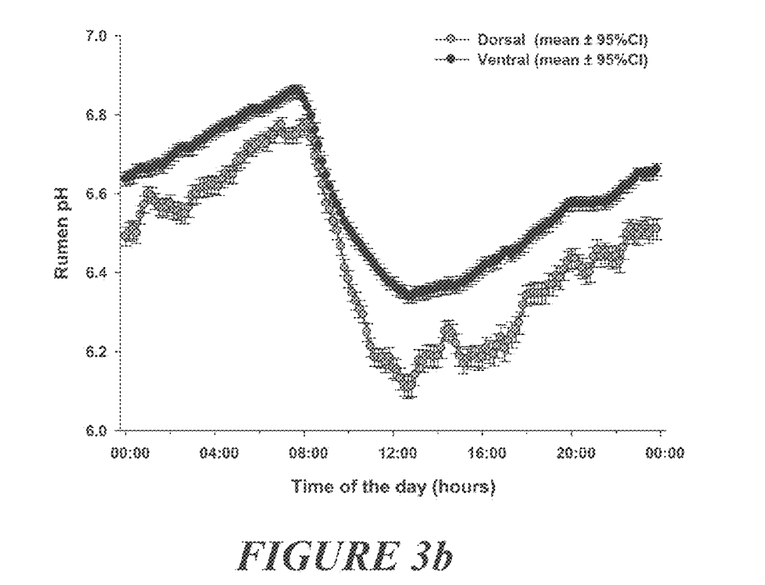
FIG. 3b is a graph obtained from the experimental work showing circadian rhythms of pH from the ventral and dorsal sac of the rumen.
Figure 3C:
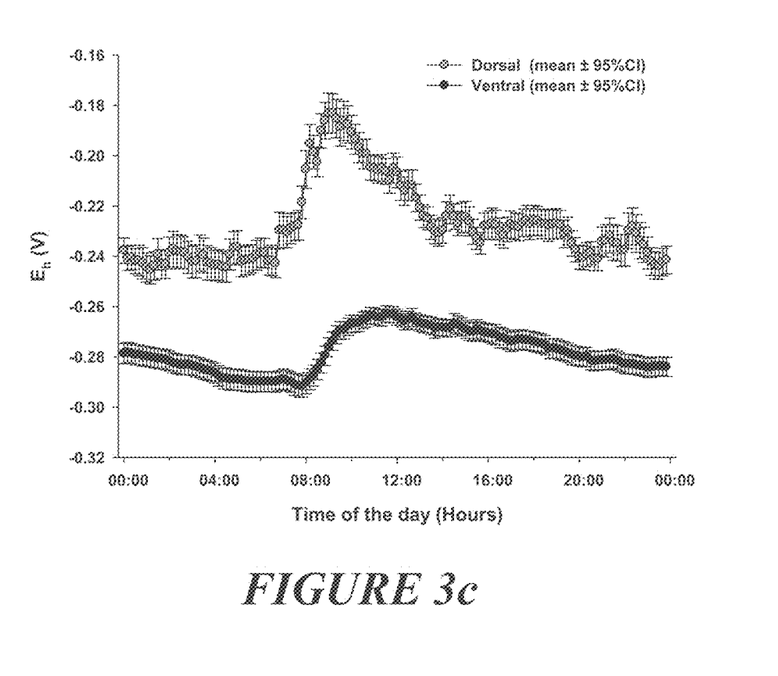
FIG. 3c is a graph obtained from the experimental work showing circadian rhythms of redox ($E_h$) from the ventral and dorsal sac of the rumen.

Measurements were compared using the following methodology: A general linear model was constructed (using JMP 8, SAS), and the main factors were described as the circadian rhythm, the week of recording and the site of recording with animals being treated as a random factor. As the drift was linear over time, the bolus was used as autoregressive ($AR_1$) covariance. Using this model a circadian rhythm (time of the days in hours) was constructed for each variable and displayed in a graphical way using the mean value every 10 minutes and 95% confidence intervals (FIGS. 3 and 4). Linear regression analysis between sites (dorsal and ventral sac) was deduced from those models and the correlation between sites was described. Paired-T test analyses were performed for the drift analysis together with descriptive statistics. FIG. 3a shows circadian rhythms of temperature from the ventral (bottom) or dorsal (top) sac of the rumen; FIG. 3b shows circadian rhythms of pH from the ventral (top) or dorsal (bottom) sac of the rumen; and. FIG. 3c shows circadian rhythms of redox ($E_h$) from the ventral (bottom) or dorsal (top) sac of the rumen. In FIGS. 3a-c values represent the mean and the 95% confidence intervals for a 10 minute interval during a daytime.

Figure 4A:
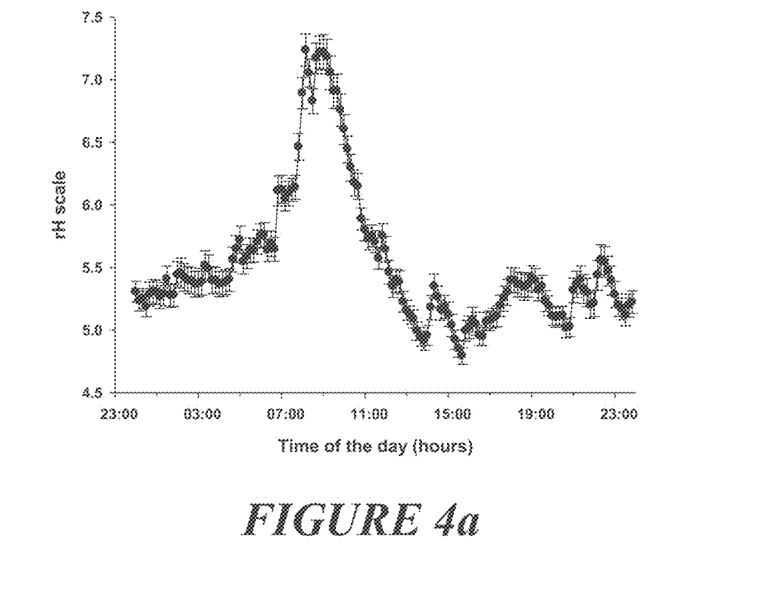
FIG. 4a is a graph obtained from the experimental work showing the circadian distribution of values of hydrogen scale (rH) obtained from the bolus of FIG. 2.
Figure 4B:
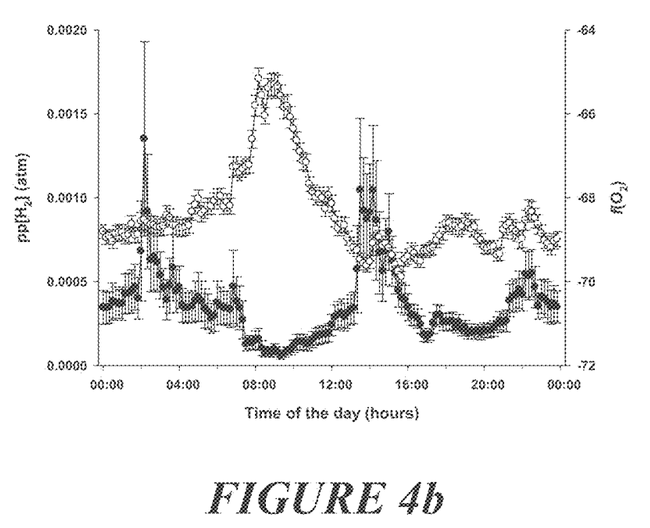
FIG. 4b is a graph obtained from the experimental work showing the circadian distribution of values of partial pressure of hydrogen and fugacity of oxygen, expressed in a logarithmic scale, obtained from the bolus of FIG. 2.
Figure 4C:
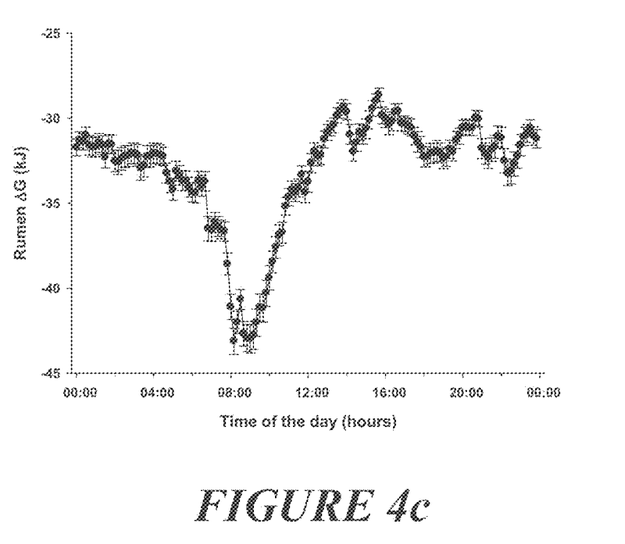
FIG. 4c is a graph obtained from the experimental work showing the circadian distribution of values of the Gibbs free energy of the system (ΔG, kJ) obtained from the bolus of FIG. 2.

FIG. 4a shows the circadian distribution of values of hydrogen scale (rH), obtained with the bolus; FIG. 4b shows the circadian distribution of values of partial pressure of hydrogen (pp[H2] in atmosphere, black) and fugacity of oxygen (Log $f(O_2)$, white), expressed in a logarithmic scale, obtained with the bolus; and FIG. 4c shows the circadian distribution of values of the Gibbs free energy of the system ($\Delta G$, kJ) obtained with the bolus. In FIGS. 4a-c values represent the mean plus or minus the 95% confidence intervals.

Results:

The drift of the pH sensors during the month of experimental work although significant was very small (0.1 pH point). Similarly the $E_h$ sensors remained very accurate during all the experiment.

The comparison between sites, dorsal and ventral sac, showed that the circadian rhythms of temperature and pH were closely related (Table 1, and FIGS. 3a and 3b). Although, differences can be seen between sites within a daily pattern, the sites tend to follow one another. The largest differences between sites were observed on the $E_h$ capacity of the ventral and dorsal sac, both compartments clearly having different $E_h$ capacities (FIG. 3c).

Differences between sites of sampling were more striking comparing the models for the parameters with a linear regression analysis between sites. This analysis clearly shows pH and temperature are highly correlated between sites (Table 1) and values obtained from the dorsal sac measurement are a good indicator of the overall pH and temperature of the rumen. However, Redox ($E_h$) of the ventral sac was only slightly correlated to the dorsal sac measurements sac ($R^2$=0.282).

TABLE 1

Equations (slope and intercept) for the relationships between dorsal (x) and ventral (y) measurements of pH, temperature and redox ($E_h$).

| Factor | Slope | intercept | Adj $R^2$ |
| --- | --- | --- | --- |
| Temperature (° C.) | 12.105 ± 0.744 | 0.683 ± 0.019 | 0.898 |
| pH | 1.474 ± 0.071 | 0.794 ± 0.011 | 0.973 |
| $E_h$ (V) | −0.215 ± 0.008 | 0.279 ± 0.037 | 0.282 |

Using the sensors onboard the bolus 150, one can calculate other valuable information from the rumen (in real-time) including hydrogen scale (rH), partial pressure of hydrogen (pp[$H_2$]), fugacity of oxygen (f($O_2$)) and Gibbs free energy of the system ($\Delta G$). Table 2 and FIGS. 4a-c also show the circadian distribution of these values.

TABLE 2

Mean values for hydrogen scale (rH), partial pressure of hydrogen (pp[$H_2$]), fugacity of oxygen (f($O_2$)) and Gibbs free energy of the system ($\Delta G$) obtained with the bolus for the rumen environment.

| | Descriptive statistics | | | | |
| --- | --- | --- | --- | --- | --- |
| Variable | Mean | Standard Error (SE) | Standard Deviation (SD) | Minimum | Maximum |
| rH scale | 5.54 | 0.009 | 2.176 | 1.23 | 18.36 |
| pp[$H_2$] (atm × $10^{-3}$) | 0.358 | 0.0058 | 1.486 | 0.000 | 58.987 |
| f(O2) | −68.4 | 0.02 | 4.31 | −78.3 | −42.9 |
| $\Delta G$(kJ) | −33.1 | 0.05 | 12.98 | −109.4 | −7.3 |

These secondary parameters are largely affected by feeding (around 8:00). The rumen environment becomes more reduced (lower rH values) as the digestion of the food progresses (FIG. 4a). Similarly, feeding increases the amount of oxygen present in the digesta (log f($O_2$) increase), but the oxygen is quickly disposed reaching the lowest values around 4 hours post feeding (FIG. 4b). Partial pressure of hydrogen (pp[$H_2$]), on the other hand, reached highest values after the nadir of oxygen (FIG. 4b). Finally, the free Gibbs energy of the rumen ($\Delta G$) decreased with feeding. Lowest values are reached within a few minutes after feeding; the highest $\Delta G$ is reached 4 hours after feeding (FIG. 4c).

Ventral sac measurements were only slightly correlated to the $E_h$ recordings from the dorsal sac (Table 1). The circadian rhythms of $E_h$ from the dorsal sac were more dynamic and variable, especially around feeding (FIG. 3c). Together, the higher temperature, $E_h$ and lower pH of the dorsal sac could be a direct consequence of higher nutrient distribution and indicative of greater metabolic activity in this compartment than in the ventral sac.

The experiment demonstrates the feasibility of using the bolus to derive thermodynamics to explain circadian changes within the rumen. FIG. 5 shows the relationship between pH and $\Delta G$, and by including the time (daily hours) it can be shown that by feeding the animals the system gets energised and $\Delta G$ falls after feeding (8:00). As fermentation progresses and bacterial activity increases, the pH drops, SCFA accumulate and the $\Delta G$ increases towards equilibrium. In other words, as the system gets energised (feeding, 8 am) the activity of the bacteria will produce work reflected in the accumulation of acid in the rumen (i.e. lower pH). As the $\Delta G$ of the rumen environment tends to equilibrium ($\Delta G$=0), bacteria activity will reach a steady state.

With the bolus 150 deployed in the correct site, the dorsal sac monitors the activity of the rumen microbiota. Consequently, the secondary parameters obtained with this bolus could give direct insight into the efficiency of fermentative processes such as SCFA and ATP formation, bacterial growth (protein formation), the optimization of fermentation by improving feeding practices (timing and supplementation), or reducing waste product such as methane and ammonia. This technology could aid in the direct and real time determination of protein and carbohydrate metabolism, predicting methane emissions and nitrogen losses, and overall improving the conversion efficiency of ruminants.

Trial 2

Method:

Ten milking fistulated cattle were fitted with bolus devices as described previously in relation to and as shown in FIG. 2 to assess the performance of the automated uploading of data from the system. The cattle were milked twice daily declining to once daily prior to being dried off. The specific purpose of the trial was to assess whether data could be gathered from the rumen without need to modify any of the animal's daily routine or management or disruption of normal production practices, which if required represents an additional cost to the producer.

One bolus was placed into the rumen of each animal through cannulae. The boluses were set to log data every five minutes and data was to be uploaded automatically by a system as described previously in relation to and as shown in FIG. 1, as each animal entered the dairy shed. Progress of the trial was monitored daily from a remote location over the internet. Data was gathered over a period of 23 days.

Results:

111,000 records were captured over a total of 338 bolus days in-vivo. 100% of the data was successfully automatically uploaded from the animals without the need for any human intervention. The trial demonstrates the feasibility of automatically gathering data from the dorsal sac of the rumen of production cattle over an extended period.

The invention claimed is:

1. A system for monitoring the process of fermentation within the rumen of one or more ruminant animals comprising:
   one or more rumen boluses each having a body comprising at or towards one end of the body opposed lateral extensions or tabs which are flexible toward the body but have memory towards a position extending outwardly of the body to retain the bolus within the dorsal sac of the rumen of the associated animal, the bolus having buoyancy within the dorsal sac against falling to the bottom of the rumen, and each bolus comprising within the body:
      a temperature sensor to provide data indicative of temperature within the rumen,
      a pH sensor to provide data indicative of pH within the rumen, and
      a redox sensor to provide data indicative of the oxidation-reduction potential within the rumen, and
      a wireless transmitter for transmitting data or derived parameters to a remote station, and
   in the or each bolus or at a remote station a processor arranged to derive from the sensor data one or more parameters indicative of the process of fermentation.

2. A system according to claim 1 wherein each bolus comprises stored in memory in the bolus an identification code unique to the individual bolus.

3. A system according to claim 1 arranged to transmit data at least once per week, at least once per day, or at least twice per day.

4. A system according to claim 3 arranged to transmit data for at least one week, for at least four weeks, for at least three months, or indefinitely.

5. A system according to claim 1 wherein the processor is located within the remote station.

6. A system according to claim 1 wherein the processor is located within the bolus.

7. A system according to claim 1 arranged to store locally in the bolus the sensor data and/or derived parameters and transmit same to the remote station when the animal comes into proximity of a receiver.

8. A system according to claim 7 wherein the receiver is located proximal to an animal milking, watering or handling station.

9. A system according to claim 1 wherein the one or more parameters includes any combination of one or more of hydrogen scale (rH), partial pressure of hydrogen ($pp[H_2]$), oxygen fugacity ($f(O_2)$) and free energy of the system ($\Delta G$).

10. A system according to claim 9 wherein the equation stored in memory for obtaining rH is:

$$rH = (E_h * 2 * F/(2.303 * R * T)) + 2 * pH$$

where:
   $E_h$=hydrogen potential (V) derived from the redox sensor data
   F=faraday's constant (96.485 kj·V$^{-1}$·mol$^{-1}$)
   R=gas constant (0.008314472 kJ·mol$^{-1}$·K$^{-1}$)
   T=temperature (K) derived from the temperature sensor data,
   rH=-log ($H_2$), and
   pH=-log ($H^+$) derived from the pH sensor data.

11. A system according to claim 10 wherein rH is indicative of the reductive or oxidative intensity of the rumen environment and the processor is arranged to output a value ranging from 0 to 42, wherein 0 represents a saturate atmosphere of hydrogen.

12. A system according to claim 9 wherein the equation stored memory for obtaining $pp[H_2]$ is:

$$pp[H_2] = 10^{-rH} \text{ (atm)}$$

where:
   $pp[H_2]$=partial pressure of hydrogen (atmospheres), and
   rH=hydrogen scale.

13. A system according to claim 9 wherein the equation stored in memory for obtaining $f(O_2)$ is:

$$\text{Log } f(O_2) = [(E_h - 0.818) * 4 * F/(2.303 * R * T)) + 4 * pH)]$$

where:
   $f(O_2)$=fugacity of oxygen gas ($p[O_2]$)
   $E_h$=hydrogen potential (V) derived from the redox sensor data
   F=faraday's constant (96.485 kJ·V$^{-1}$·mol$^{-1}$)
   R=gas constant (0.008314472 kJ·mol$^{-1}$·K$_{-1}$)
   T=temperature (K) derived from the temperature sensor data, and
   pH=-log ($H^+$) derived from the pH sensor data.

14. A system according to claim 9 wherein the equation stored in memory for obtaining $\Delta G$ is:

$$\Delta G = 2.303 * R * T * rH$$

where:
   $\Delta G$=the free energy of the system (kJ/mol$^{-1}$)
   R=gas constant (0.008314472 kJ·mol$^{-1}$·K$^{-1}$)
   T=temperature (K) derived from the temperature sensor data, and
   rH=the hydrogen scale.

15. A system according to claim 1 wherein the rumen bolus(es) also comprise any one or more of:
   a pressure sensor for providing data indicative of the pressure within the rumen,
   a conductivity sensor for providing data indicative of the conductivity within the rumen,
   a potassium sensor for providing data indicative of the concentration of potassium within the rumen,
   a chloride sensor for providing data indicative of the concentration of chloride within the rumen
   a sodium sensor for providing data indicative of the concentration of sodium within the rumen, and an ammonium sensor for providing data indicative of the concentration of ammonia within the rumen.

16. A method for monitoring the process of fermentation in the rumen of one or more ruminant animals comprising the steps of:

providing a bolus within the dorsal sac of the rumen of the or each animal, the bolus having a body comprising at or towards one end of the body opposed lateral extensions or tabs which are flexible towards the body but have memory towards a position extending outwardly of the body to retain the bolus within the dorsal sac of the rumen of the associated animal, the bolus having buoyancy within the dorsal sac against falling to the bottom of the rumen, and each bolus comprising within the body:

a temperature sensor to provide data indicative of the temperature within the rumen, a pH sensor to provide data indicative of the pH within the rumen, and a redox sensor to provide data indicative of the oxidation-reduction potential within the rumen, and sensing via the bolus a combination of temperature, pH, and oxidation-reduction potential within the dorsal sac of the or each rumen, wirelessly transmitting from the bolus the sensed data or derived parameters to a remote receiver, and in a processor in the bolus or at a remote station deriving from the sensor data one or more parameters indicative of the process of fermentation.

17. A rumen bolus for monitoring the process of fermentation of a ruminant animal, comprising:

a body comprising at or towards one end of the body opposed lateral extensions or tabs which are flexible towards the body but have memory towards a position extending outwardly of the body to retain the bolus within the dorsal sac of the rumen of the animal, the bolus having buoyancy within the dorsal sac against falling to the bottom of the rumen, and housed within the body of the bolus:

a temperature sensor to provide data indicative of the temperature within the rumen, a pH sensor to provide data indicative of the pH within the rumen, a redox sensor to provide data indicative of the oxidation-reduction potential within the rumen, and a wireless transmitter to transmit sensor data or one or more parameters derived by processing the sensor data, or both, to a remote station, wherein when the wireless transmitter is operable to transmit the one or more derived parameters, the one or more parameters are derived in a processor located in the bolus.

18. A system according to claim 1 wherein the processor is arranged to derive from the sensor data one or more parameters indicative of animal digestive efficiency.

19. A method according to claim 16 wherein the step of deriving from the sensor data one or more parameters indicative of the process of fermentation, comprises deriving from the sensor data one or more parameters indicative of animal digestive efficiency.

20. A system according to claim 1 comprising multiple rumen boluses for a group of animals.

* * * * *